(12) United States Patent
Theuss et al.

(10) Patent No.: US 10,241,088 B2
(45) Date of Patent: Mar. 26, 2019

(54) PHOTO-ACOUSTIC GAS SENSOR MODULE HAVING LIGHT EMITTER AND DETECTOR UNITS

(71) Applicant: Infineon Technologies AG, Neubiberg (DE)

(72) Inventors: Horst Theuss, Wenzenbach (DE); Gottfried Beer, Nittendorf (DE); Sebastian Beer, Regensburg (DE); Alfons Dehe, Reutlingen (DE); Franz Jost, Stuttgart (DE); Stefan Kolb, Unterschleissheim (DE); Guenther Ruhl, Regensburg (DE); Rainer Markus Schaller, Saal a.d. Donau (DE)

(73) Assignee: Infineon Technologies AG, Neubiberg (DE)

( * ) Notice: Subject to any disclaimer, the term of this patent is extended or adjusted under 35 U.S.C. 154(b) by 132 days.

(21) Appl. No.: 15/136,469

(22) Filed: Apr. 22, 2016

(65) Prior Publication Data

US 2016/0313288 A1   Oct. 27, 2016

(30) Foreign Application Priority Data

Apr. 24, 2015   (DE) .......................... 10 2015 106 373

(51) Int. Cl.
*G01N 29/24*        (2006.01)
*G01N 29/032*       (2006.01)

(52) U.S. Cl.
CPC ....... *G01N 29/2425* (2013.01); *G01N 29/032* (2013.01); *G01N 2291/021* (2013.01)

(58) Field of Classification Search
CPC ....... G01N 21/1702; G01N 2021/1704; G01N 29/2425; G01N 29/2418; G01N 2201/0637
See application file for complete search history.

(56) References Cited

U.S. PATENT DOCUMENTS

| | | | | |
|---|---|---|---|---|
| 3,820,901 A | * | 6/1974 | Kreuzer | G01N 21/314 250/345 |
| 3,938,365 A | * | 2/1976 | Dewey, Jr. | G01N 21/1702 356/330 |
| 4,591,721 A | * | 5/1986 | Wong | G01J 3/433 250/373 |
| 4,605,313 A | * | 8/1986 | Kebabian | G01N 21/3504 250/343 |

(Continued)

FOREIGN PATENT DOCUMENTS

| | | |
|---|---|---|
| CN | 102279156 A | 12/2011 |
| CN | 103180698 A | 6/2013 |

(Continued)

*Primary Examiner* — David A Rogers
(74) *Attorney, Agent, or Firm* — Murphy, Bilak & Homiller, PLLC

(57) ABSTRACT

A photo-acoustic gas sensor includes a light emitter unit having a light emitter configured to emit a beam of light pulses with a predetermined repetition frequency and a wavelength corresponding to an absorption band of a gas to be sensed, and a detector unit having a microphone. The light emitter unit is arranged so that the beam of light pulses traverses an area configured to accommodate the gas. The detector unit is arranged so that the microphone can receive a signal oscillating with the repetition frequency.

9 Claims, 17 Drawing Sheets

(56) References Cited

U.S. PATENT DOCUMENTS

| | | | | |
|---|---|---|---|---|
| 4,622,845 | A | * | 11/1986 | Ryan ................. G01N 21/1702 356/432 |
| 4,740,086 | A | * | 4/1988 | Oehler ............... G01N 21/1702 250/343 |
| 4,817,413 | A | * | 4/1989 | Asano ................ G01N 21/1702 73/24.02 |
| 4,818,882 | A | * | 4/1989 | Nexo ................. G01N 21/1702 250/343 |
| RE35,355 | E | * | 10/1996 | Ryan ........................ G01J 3/26 250/343 |
| 5,616,826 | A | | 4/1997 | Pellaux et al. |
| 5,753,797 | A | * | 5/1998 | Forster ............... G01N 21/1702 250/343 |
| 5,841,017 | A | | 11/1998 | Baraket et al. |
| 6,006,585 | A | * | 12/1999 | Forster ............... G01N 21/1702 250/343 |
| 6,222,190 | B1 | * | 4/2001 | Bernstein ................. G01J 5/42 250/343 |
| 6,244,101 | B1 | * | 6/2001 | Autrey ............... G01N 21/1702 356/432 |
| 6,344,647 | B1 | * | 2/2002 | Jourdain ............ G01N 21/1702 250/339.07 |
| 6,662,627 | B2 | * | 12/2003 | Arnott ................ G01N 21/1702 356/438 |
| 6,725,704 | B2 | * | 4/2004 | Lange ................. G01N 21/1702 73/23.2 |
| 7,242,479 | B2 | * | 7/2007 | Moeckli ............. G01N 21/1702 250/339.04 |
| 8,240,189 | B2 | * | 8/2012 | Myrick .............. G01N 21/3504 73/24.02 |
| 8,434,366 | B2 | | 5/2013 | Hung et al. |
| 8,448,495 | B2 | * | 5/2013 | Breviere ................. G01N 1/40 250/343 |
| 8,594,507 | B2 | | 11/2013 | Youngner et al. |
| 8,695,402 | B2 | * | 4/2014 | Thorson ............. G01N 21/1702 73/24.02 |
| 8,709,820 | B2 | * | 4/2014 | Marzouk ................ G01N 30/00 422/51 |
| 9,513,261 | B2 | * | 12/2016 | Dehe ................. G01N 29/2418 |
| 9,523,637 | B2 | * | 12/2016 | Myrick .............. G01N 21/3504 |
| 2005/0160791 | A1 | * | 7/2005 | Kung .................... G01N 21/05 73/24.02 |
| 2006/0009707 | A1 | * | 1/2006 | Daniels .................. A61B 5/083 600/532 |
| 2006/0126070 | A1 | * | 6/2006 | Kauppinen ........ G01N 21/1702 356/432 |
| 2007/0279633 | A1 | * | 12/2007 | Yi ........................ G01N 21/031 356/432 |
| 2008/0276687 | A1 | | 11/2008 | Myrick et al. |
| 2011/0032516 | A1 | * | 2/2011 | Zhou ..................... G01N 21/39 356/73 |
| 2012/0000271 | A1 | * | 1/2012 | Fritz .................. G01N 21/0303 73/24.02 |
| 2012/0103065 | A1 | * | 5/2012 | Muehleisen .............. G01J 3/18 73/24.02 |
| 2012/0151994 | A1 | * | 6/2012 | Hung ................. G01N 21/1702 73/24.02 |
| 2012/0279281 | A1 | * | 11/2012 | Myrick .............. G01N 21/3504 73/24.02 |
| 2012/0318041 | A1 | * | 12/2012 | Youngner .......... G01N 21/1702 73/24.02 |
| 2013/0208280 | A1 | * | 8/2013 | Bitter .................. G01N 21/274 356/435 |
| 2015/0101395 | A1 | * | 4/2015 | Dehe ................. G01N 29/2418 73/24.02 |
| 2015/0123000 | A1 | * | 5/2015 | Sagberg ............ G01N 21/3504 250/341.1 |
| 2015/0260981 | A1 | * | 9/2015 | Sano ........................ G01J 3/26 359/578 |
| 2016/0282259 | A1 | * | 9/2016 | Kolb ................... G01N 29/022 |

FOREIGN PATENT DOCUMENTS

| | | | |
|---|---|---|---|
| DE | 10051691 A1 | 6/2001 | |
| DE | 102006048839 A1 | 4/2008 | |
| DE | 102014114672 A1 | 4/2015 | |
| EP | 1582857 A1 | 10/2005 | |
| GB | 2358245 A | 7/2001 | |
| GB | 2497296 A * | 6/2013 | ......... G01N 21/3504 |
| GB | 2497296 A * | 6/2013 | ......... G01N 21/3504 |
| WO | 2004008113 A1 | 1/2004 | |
| WO | 2008046824 A1 | 4/2008 | |

* cited by examiner

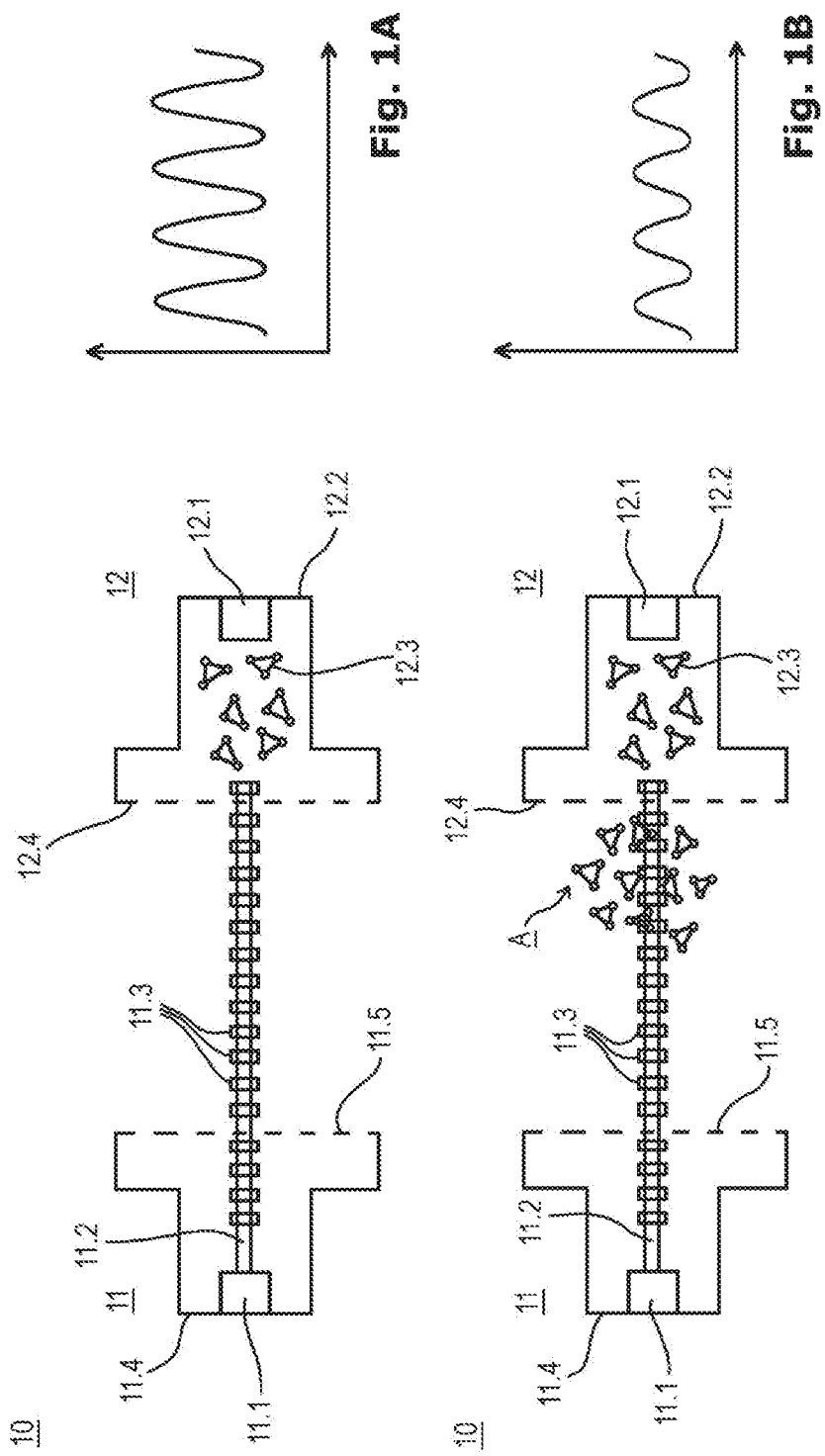

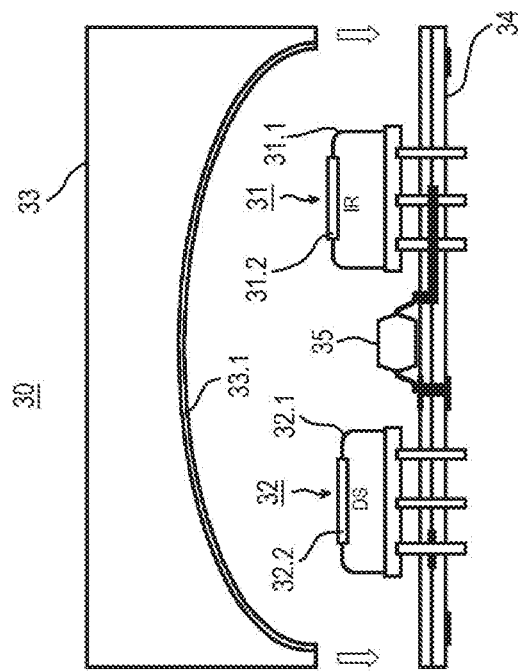
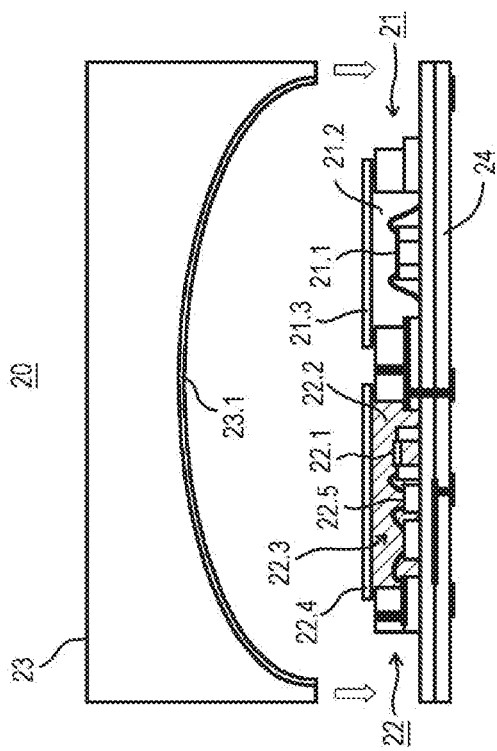
Fig. 2B
Fig. 2A

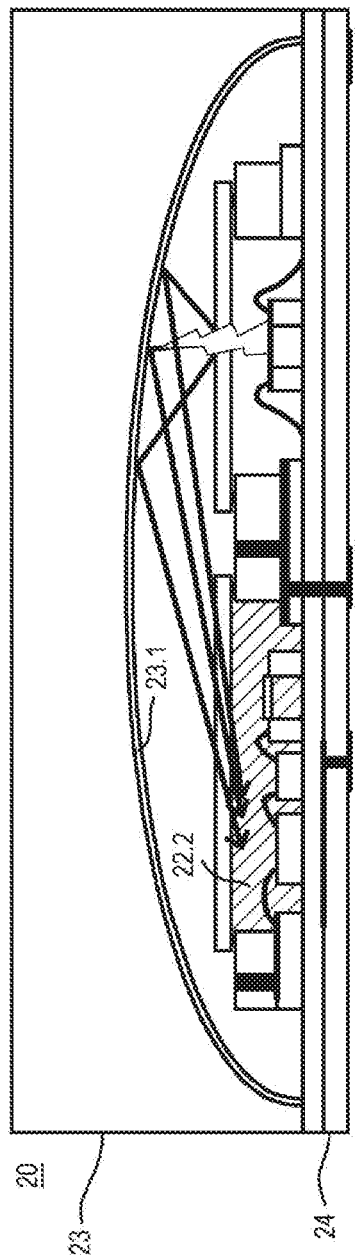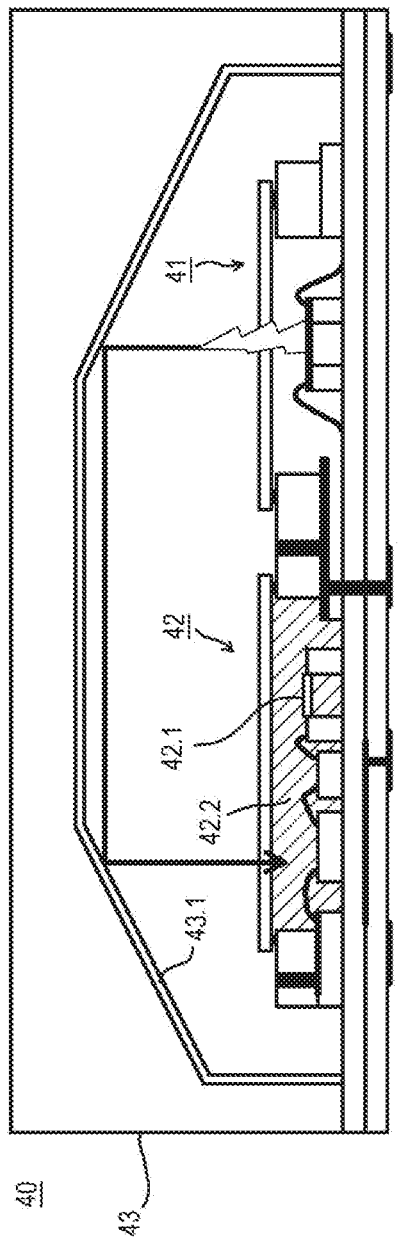

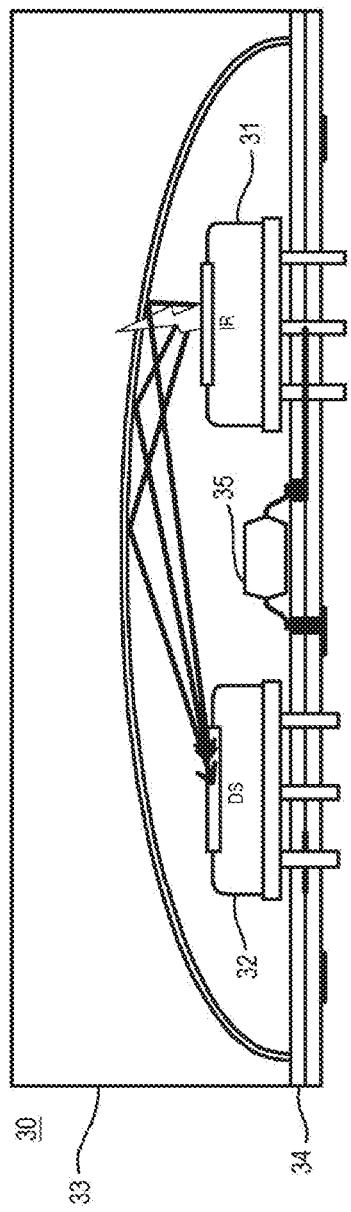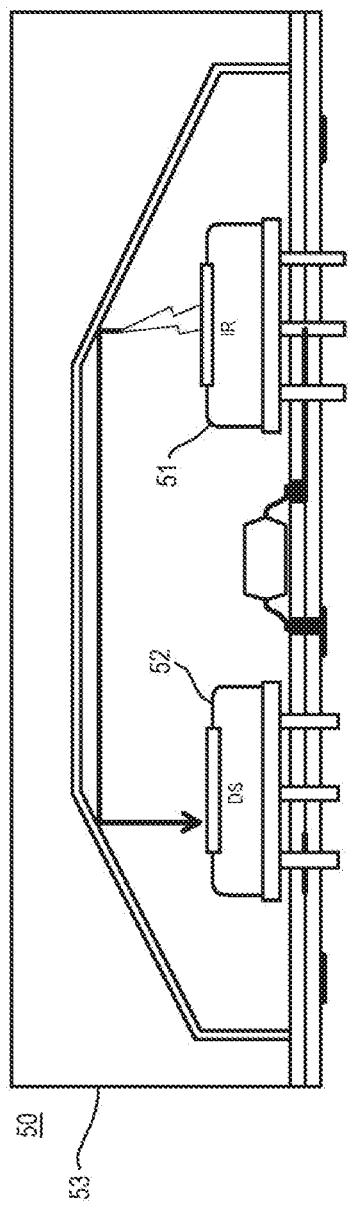

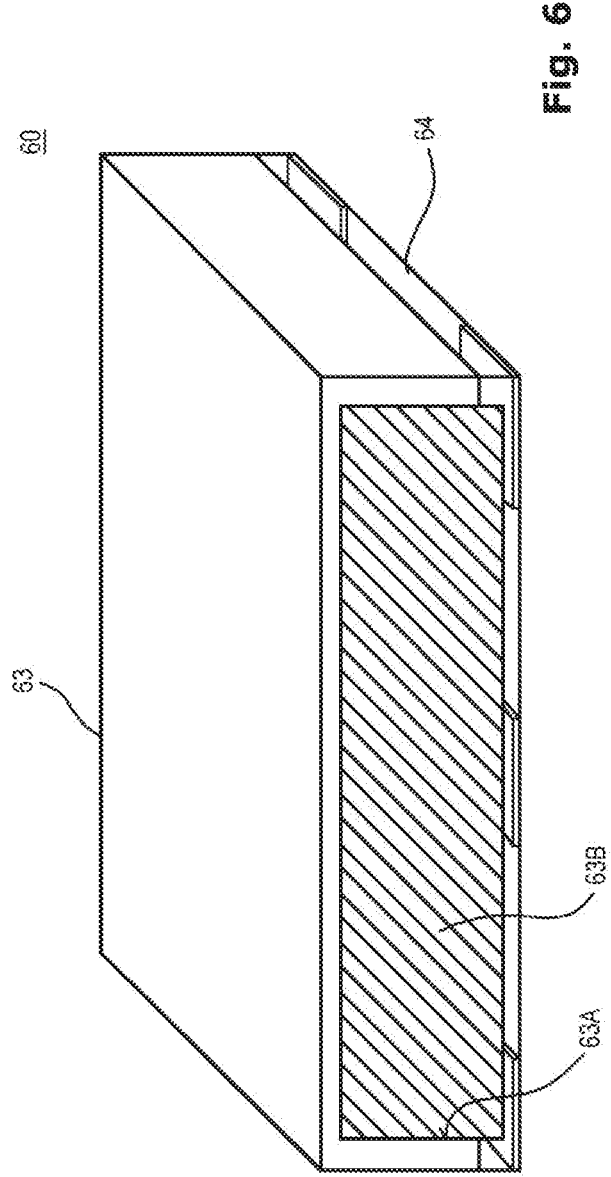

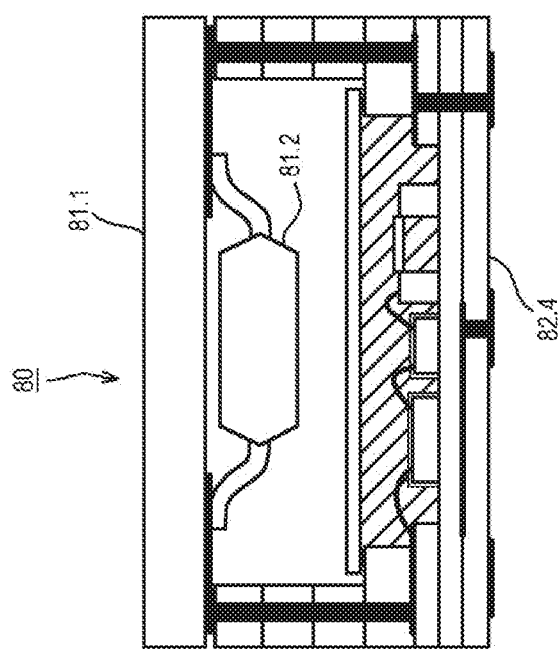
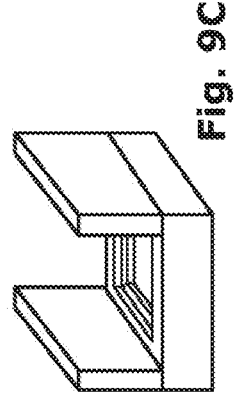
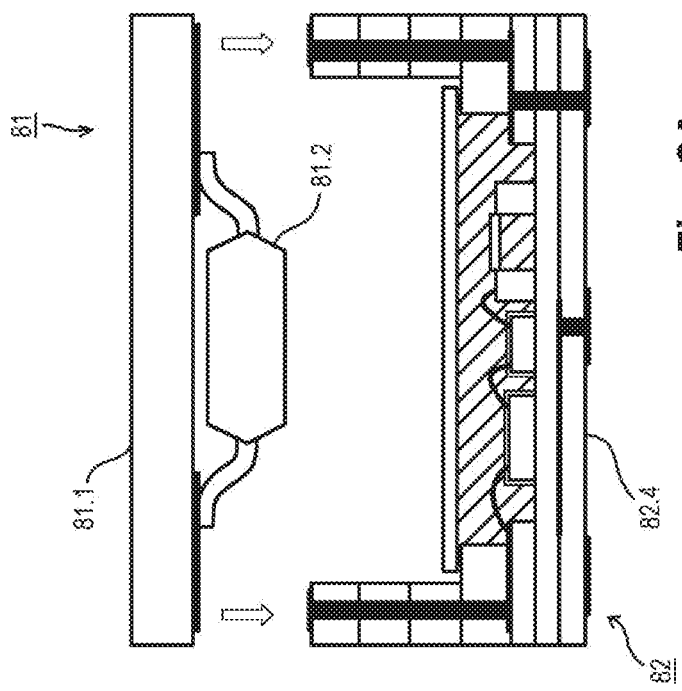
Fig. 9A
Fig. 9B
Fig. 9C

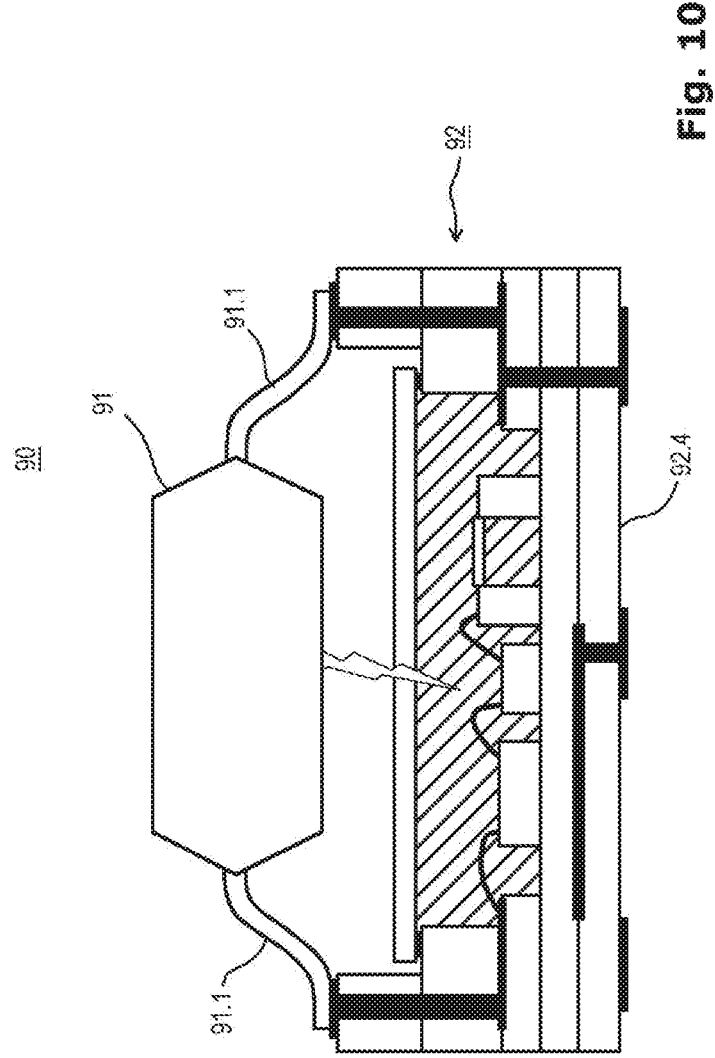

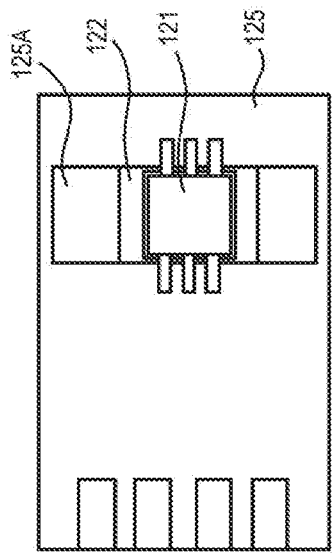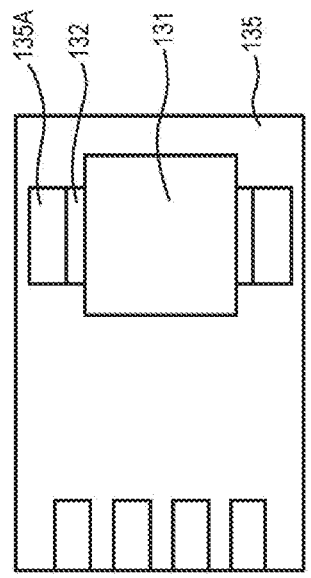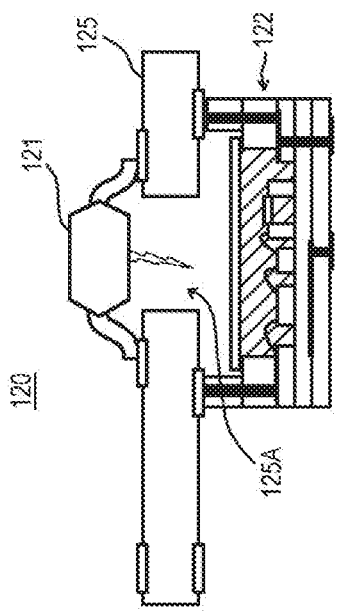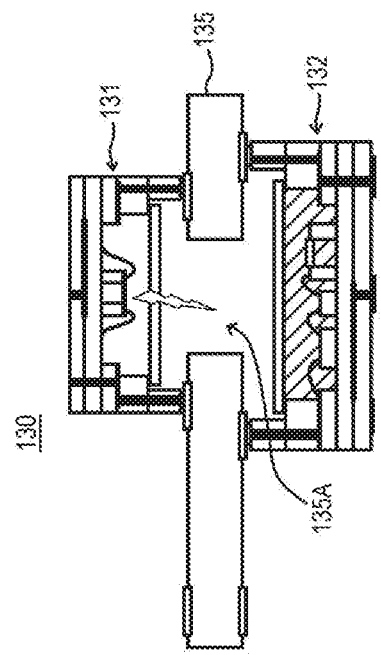
Fig. 12A
Fig. 12B

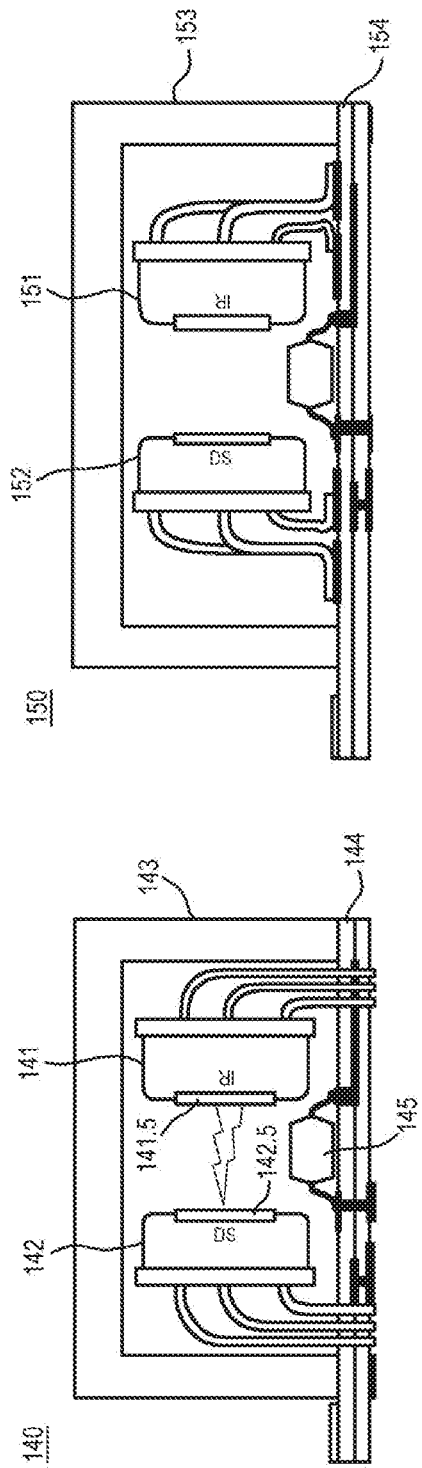

PHOTO-ACOUSTIC GAS SENSOR MODULE HAVING LIGHT EMITTER AND DETECTOR UNITS

TECHNICAL FIELD

The present application relates to a photo-acoustic gas sensor and to a photo-acoustic gas sensor module.

BACKGROUND

In the past many types of gas detection devices have been developed in order to detect that the atmosphere or the environment contains potentially harmful or hazardous components and, if possible, to provide a warning thereof to a person. The proper function of gas detectors can be of great importance in many applications, especially when these detectors are used for insuring the safety of working personal. Besides that, the space consumption of gas detectors also becomes more and more important as the size of many apparatuses and instruments are continuously getting smaller. This overall trend of miniaturization creates a need to develop more compact gas sensors which can be easily incorporated into existing apparatuses or instruments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIGS. 1A and 1B show a photo-acoustic gas sensor according to an example, also indicating the measurement principle.

FIGS. 2A and 2B show schematic cross-sectional side view representations of an example of a photo-acoustic gas sensor comprising a ceramic substrate and a sensor housing (shown lifted) according to a first aspect, and an example of a photo-acoustic gas sensor comprising a printed circuit board substrate and a sensor housing (shown lifted) according to a second aspect.

FIGS. 3A and 3B show schematic cross-sectional side view representations of an example of a photo-acoustic gas sensor according to the first aspect comprising a housing having an ellipsoidal inner wall, and an example of a photo-acoustic gas sensor according to the first aspect comprising a housing having a polygonal inner wall.

FIGS. 4A and 4B show schematic cross-sectional side view representations of an example of a photo-acoustic gas sensor according to the second aspect comprising a housing having an ellipsoidal inner wall, and an example of a photo-acoustic gas sensor according to the second aspect comprising a housing having a polygonal inner wall.

FIG. 6 shows a perspective representation of an example of a photo-acoustic gas sensor according to the first aspect comprising a sensor housing having a protective cover covering the opening for preventing penetration of humidity and/or particles and enabling only penetration of defined gases.

FIGS. 9A through 9C show schematic cross-sectional side view representations of an example of a photo-acoustic gas sensor according to the first aspect, wherein the detector is disposed on a ceramic substrate and the emitter is disposed on another substrate, the modules shown before being mounted together, the gas sensor shown in an assembled state, and a perspective representation of the detector module.

FIG. 10 shows a schematic cross-sectional side view representation of an example of a photo-acoustic gas sensor according to the first aspect, wherein the detector is disposed on a ceramic substrate and the emitter is configured in the form of a package the leads of which being attached to the ceramic substrate.

FIGS. 12A and 12B show schematic cross-sectional side view representations and corresponding top view representations of examples of photo-acoustic gas sensors according to the first aspect, wherein the detector is mounted on a ceramic substrate and emitter and detector are both connected to an intermediate substrate, wherein in the first example the emitter is configured as a packaged device, and wherein in the second example the emitter is mounted on a ceramic substrate.

FIGS. 13A through 13C show schematic cross-sectional side view representations of examples of photo-acoustic gas sensors according to the second aspect, wherein the emitter and the detector are arranged face-to-face with each other and each comprise external leads, wherein in the first example the leads are through-hole connected to a printed circuit board, wherein in the second example the leads are surface mount connected to a printed circuit board, and a perspective representation of either one of the examples.

DETAILED DESCRIPTION

Figure 5B:
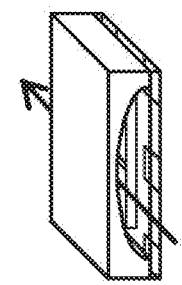
FIGS. 5A and 5B show a perspective representation of an example of a photo-acoustic gas sensor according to the first aspect comprising a sensor housing (shown lifted) having an ellipsoidal inner wall, and the same photo-acoustic gas sensor with the housing attached to the substrate and indicating the gas flow.

The aspects and embodiments are now described with reference to the drawings, wherein like reference numerals are generally utilized to refer to like elements throughout. In the following description, for purposes of explanation, numerous specific details are set forth in order to provide a thorough understanding of one or more aspects of the embodiments. It may be evident, however, to one skilled in the art that one or more aspects of the embodiments may be practiced with a lesser degree of the specific details. In other instances, known structures and elements are shown in schematic form in order to facilitate describing one or more aspects of the embodiments. It is to be understood that other embodiments may be utilized and structural or logical changes may be made without departing from the scope of the present invention. It should be noted further that the drawings are not to scale or not necessarily to scale.

In the following detailed description, reference is made to the accompanying drawings, which form a part hereof, and in which is shown by way of illustration specific aspects in which the invention may be practiced. In this regard, directional terminology, such as "top", "bottom", "front", "back", etc., may be used with reference to the orientation of the figures being described. Since components of described devices may be positioned in a number of different orientations, the directional terminology may be used for purposes of illustration and is in no way limiting. It is understood that other aspects may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

As employed in this specification, the terms "bonded", "attached", "connected", "coupled" and/or "electrically connected/electrically coupled" are not meant to mean that the elements or layers must directly be contacted together; intervening elements or layers may be provided between the "bonded", "attached", "connected", "coupled" and/or "electrically connected/electrically coupled" elements, respectively. However, in accordance with the disclosure, the above-mentioned terms may, optionally, also have the specific meaning that the elements or layers are directly contacted together, i.e. that no intervening elements or layers are provided between the "bonded", "attached", "connected", "coupled" and/or "electrically connected/electrically coupled" elements, respectively.

Further, the word "over" used with regard to a part, element or material layer formed or located "over" a surface may be used herein to mean that the part, element or material layer be located (e.g. placed, formed, deposited, etc.) "indirectly on" the implied surface with one or more additional parts, elements or layers being arranged between the implied surface and the part, element or material layer. However, the word "over" used with regard to a part, element or material layer formed or located "over" a surface may, optionally, also have the specific meaning that the part, element or material layer be located (e.g. placed, formed, deposited, etc.) "directly on", e.g. in direct contact with, the implied surface.

In addition, while a particular feature or aspect of an embodiment may be disclosed with respect to only one of several implementations, such feature or aspect may be combined with one or more other features or aspects of the other implementations as may be desired and advantageous for any given or particular application. Furthermore, to the extent that the terms "include", "have", "with" or other variants thereof are used in either the detailed description or the claims, such terms are intended to be inclusive in a manner similar to the term "comprise". The terms "coupled" and "connected", along with derivatives may be used. It should be understood that these terms may be used to indicate that two elements co-operate or interact with each other regardless whether they are in direct physical or electrical contact, or they are not in direct contact with each other. Also, the term "exemplary" is merely meant as an example, rather than the best or optimal. The following detailed description, therefore, is not to be taken in a limiting sense, and the scope of the present invention is defined by the appended claims.

The examples of detector modules described herein may comprise microphone chips. The microphone chips may be comprised of semiconductor chips. The semiconductor chips can be manufactured on the basis of a specific semiconductor material, for example Si, SiC, SiGe, GaAs, GaN, AlGaAs, but can also manufactured on the basis of any other semiconductor material and, furthermore, may contain inorganic and/or organic materials that are not semiconductors, such as for example insulators, plastics or metals. The microphone chips can be fabricated by MEMS (micro-opto electro-mechanical) technology.

The examples of a photo-acoustic gas sensor may comprise an encapsulant or encapsulating material having one or more of the chips embedded therein. The encapsulating material can be any electrically insulating material like, for example, any kind of molding material, any kind of resin material, or any kind of epoxy material. The encapsulating material can also be a polymer material, a polyimide material, a thermoplast material, a silicone material, a ceramic material, and a glass material. The encapsulating material may also comprise any of the above-mentioned materials and further include filler materials embedded therein like, for example, thermally conductive increments. These filler increments can be made of AlO or $Al_2O_3$, AlN, BN, or SiN, for example. Furthermore the filler increments may have the shape of fibers and can be made of carbon fibers or nanotubes, for example.

FIGS. 1A and 1B show an example of a photo-acoustic gas sensor in the left-sided diagrams which together with the right-sided diagrams illustrate the working principle of the photo-acoustic gas sensor. The photo-acoustic gas sensor 10 of FIGS. 1A and 1B comprises a light emitter unit 11 comprising a light emitter 11.1 configured to emit a beam 11.2 of light pulses 11.3 with a predetermined repetition frequency and a wavelength corresponding to an absorption band of a gas to be sensed. The photo-acoustic gas sensor 10 further comprises a detector unit 12 comprising a microphone 12.1. The light emitter unit 11 is arranged so that the beam 11.2 of light pulses 11.3 traverses an area A configured to accommodate the gas and the detector unit 12 is arranged so that the microphone 12.1 can receive a signal oscillating with the repetition frequency. The reference signs 12.2, 12.3 and 12.4 designate a detector module housing, a reference gas, and a light inlet window, respectively, which are optional elements of the photo-acoustic sensor 10 of FIGS. 1A and 1B.

The light pulses modulated with the repetition frequency will be absorbed by the gas and generate a local pressure pulse which produces a characteristic signal in the microphone. The absorption is specific for the gas, in particular it corresponds to a specific transition in its characteristic rotation-vibration spectrum, so that, by applying appropriate excitation frequencies, a selective photo-acoustic gas sensor can be built. A particular challenge is to construct a compact, miniaturized photo-acoustic gas sensor which can be easily handled, transported or mounted on different sorts of substrates.

According to an example of the photo-acoustic gas sensor 10 of FIGS. 1A and 1B, the detector unit 12 comprises a detector unit housing 12.2, wherein the microphone 12.1 is disposed in the detector unit housing 12.2 and a reference gas, indicated by reference sign 12.3, is enclosed in the detector unit housing 12.2, the reference gas 12.3 being of the same species as the gas to be sensed wherein the latter is provided in the area A. According to a further example thereof, the reference gas 12.3 is hermetically sealed in the detector unit housing 12.2 and the detector unit housing 12.2 comprises at a side facing the emitter module a light entrance window 12.4 which is transmissive for light emitted by the light emitter 11.1. The gas 12.3 being hermetically sealed in the housing 12.2 can thus be designated as a reference gas or the inner volume of the detector unit housing 12.2 can be designated as a reference volume. The gas to be sensed is disposed in the area A, in particular within a light path between the emitter module 11 and the detector module 12. The measurement principle is thus configured in such a way that in a case where no gas is present to be sensed in the area A, in particular in the light path between the emitter module 11 and the light entrance window 12.4 of the detector module 12, the light pulses enter into the reference volume without any attenuation so that the signal measured and delivered by the microphone 12.1 will be maximum as can be seen in the time diagram of FIG. 1A. On the other hand, if there is gas present to be sensed in the area A, in particular in the light path between the emitter module 11 and the light entrance window 12.4 of the detector module 12, the light pulses will be attenuated so that light pulses of less intensity will enter the reference volume resulting in a decrease of the signal measured and delivered by the microphone 12.1 as indicated in the time diagram of FIG. 1B. Hence in the measurement variant illustrated in FIGS. 1A and 1B, the signal oscillating with the repetition frequency and detected by the microphone emanates from the reference gas. The presence of a gas in area A is indicated by a decrease of the signal strength detected by the microphone 12.1.

According to another example of the photo-acoustic gas sensor, there is no reference gas enclosed in a detector module housing and instead there is only the gas to be sensed present in the area A, in particular in a light path between the emitter module and the microphone. In this case the microphone will not detect and output any signal if no gas to be sensed is present in the light path between the emitter module and the detector module. On the other hand, if gas to be sensed is present in the area A, in particular in the light path between the emitter module and the detector module, the microphone will detect and output a signal the strength of which depends on the amount or density of gas present in area A. Hence in this alternative measurement variant the signal oscillating with the repetition frequency and detected by the microphone emanates from the gas itself. The presence of a gas in area A is indicated by an increase of the signal strength detected by the microphone 12.1. Consequently in this alternative variant a positive signal will be obtained in case of the presence of a gas to be sensed.

According to an example of the photo-acoustic gas sensor 10 of FIGS. 1A and 1B, the repetition frequency of the light pulses lies within an audio frequency range or within a frequency range from 1 Hz to 10 kHz, in particular from 1 Hz to 1 kHz, wherein a typical frequency range is from 1 Hz to 100 Hz corresponding to a pulse duration range from 0.01 s to 1s.

According to an example of the photo-acoustic gas sensor 10 of FIGS. 1A and 1B, the light emitted by the light emitter 11.1 may comprise any desired wavelength or wavelength range in the visible or non-visible spectrum. In particular, the light emitter unit 11 is configured to emit only light of a pre-selected wavelength corresponding to the absorption band of the gas to be sensed.

According to an example of the photo-acoustic gas sensor 10 of FIGS. 1A and 1B, the light emitter 11.1 comprises one or more of a broad-band emitter, a narrow-band emitter, a coherent light emitter, a non-coherent light emitter, a blackbody radiator, a lamp, a heated resistor, a light emitting diode (LED), or a laser, in particular laser diode. According to an example thereof, in case that the light emitter 11.1 comprises a broad-band emitter, the light emitter unit 11 may comprise an optical filter disposed in front of the light emitter 11.1, the optical filter being configured to allow to pass through light of a pre-selected wavelength of the light emitted by the light emitter 11.1. If the light emitter module 11 comprises a light emitter module housing 11.4 and a light outlet window 11.5 disposed in a wall of the light emitter unit housing 11.4, the optical filter can be applied onto the light outlet window 11.5 or it can even be identical with the light outlet window 11.5.

According to an embodiment of the photo-acoustic gas sensor 10 of FIGS. 1A and 1B, the light emitter unit 11 comprises a tunable wavelength emission range. The tuning of the wavelength of the emitted light pulses depends on the sort of light emitter 11.1 employed. If, for example, the light emitter 11.1 is a narrow-band light source like a light emitting diode (LED) or a laser diode, the tuning of the emission wavelength can be accomplished by directly controlling the light emitter 11.1. If, however, the light emitter 11.1 is a broad-band light emitter, the emitted light pulses are filtered by an optical filter, a wavelength tunable optical filter like, e.g. a Fabry-Perot filter, could be employed so that the transmission band of the optical filter could be adjusted by appropriate means. One advantage of a tunable wavelength emission range is that in principle different sorts of gases could be detected.

According to an example of the photo-acoustic gas sensor 10 of FIGS. 1A and 1B, the light emitter unit 11 is configured to emit a beam of light pulses of infrared light of a wavelength corresponding to an energy of a rotational or vibrational band or transition of a molecule of the gas to be sensed.

According to an example of the photo-acoustic gas sensor 10 of FIGS. 1A and 1B, the gas to be sensed is one of $CO_2$, $NO_x$, $H_2O$, $O_2$, $N_2$, $CH_4$ or alcohol.

According to an example of the photo-acoustic gas sensor 10 of FIGS. 1A and 1B, the light emitter unit 11 comprises a light emitter unit housing 11.4, wherein the light emitter 11.1 is disposed in the light emitter unit housing 11.4 and the light emitter unit housing 11.4 comprises a light outlet window 11.5 in a wall thereof. As already outlined above, the light outlet window 11.5 should have a transmission characteristic which allows to pass through the desired wavelength of the light emitted by the light emitter 11.1. According to a further example thereof, the light outlet window 11.5 could be designed as an optical filter for filtering the desired wavelength or such an optical filter could be attached to the light outlet window 11.5.

According to an example of the photo-acoustic gas sensor 10 of FIGS. 1A and 1B, the light emitter unit 11 and the detector unit 12 are disposed on a common substrate. Specific examples thereof will be shown further below.

According to an example of the photo-acoustic gas sensor 10 of FIGS. 1A and 1B, the light emitter unit 11 and the detector unit 12 are disposed in a face-to-face relationship which means, for example, that a light outlet window 11.5 of the emitter module 11 and a light inlet window 12.4 of the detector module 12 are disposed in a face-to-face relationship as shown in FIGS. 1A and 1B. Further specific examples thereof will be shown further below.

According to an example of the photo-acoustic gas sensor 10 of FIGS. 1A and 1B, the sensor further comprises a sensor housing, wherein the light emitter unit and the detector unit are disposed in or attached to the sensor housing. According to a further example thereof, the sensor housing comprises a wall having an inner surface which is reflective for light emitted by the light emitter unit. According to a further example thereof, the wall comprises an ellipsoidal geometry, wherein the light emitter and the microphone are disposed in the respective focus points of the ellipsoid. Specific examples thereof will be shown further below.

According to a further example, the sensor housing comprises a gas inlet opening. According to a further example thereof, the gas inlet opening is covered by a porous foil configured to enable penetration of the gas to be sensed but to prevent penetration of one or more of humidity and particles. Specific examples thereof will be shown further below.

According to an example of the photo-acoustic gas sensor 10 of FIGS. 1A and 1B, the detector module 12 comprises one or more further electronic devices like, for example, a logic integrated circuit chip, an ASIC chip, etc. Specific examples thereof will be shown further below.

According to an example of the photo-acoustic gas sensor 10 of FIGS. 1A and 1B, the photo-acoustic gas sensor is configured as a photo-acoustic sensor module which is configured as a surface mount device or a through-hole mount device. Specific examples thereof will be shown further below.

FIGS. 2A and 2B show two different examples of photo-acoustic gas sensor modules.

The photo-acoustic gas sensor module 20 of FIG. 2A comprises an emitter module 21, a detector module 22, and a sensor housing 23 covering the light emitter module 21 and the detector module 22. The sensor housing 23 comprises an opening (not shown in FIGS. 2A and 2B, see for example FIGS. 5A and 5B) for allowing atmospherical gas to enter the interior of the photo-acoustic gas sensor 20. The emitter module 21 and the detector module 22 are mounted on a common ceramic substrate 24 comprising a plurality of layers disposed one above the other and electrical via connections connected with the emitter module 21 and the detector module 22. The emitter module 21 comprises a light emitter 21.1 disposed within a cavity 21.2, wherein the cavity 21.2 comprises a recess area formed in the substrate 24, the recess area being laterally confined by a laterally closed elevation of the substrate 24, the elevation having a coplanar upper surface on which a light outlet window 21.3 is disposed. The light emitter 21.1 may be a MEMS-based resistor, diode, laser, lamp or any other coherent or non-coherent light source. It may be a completed, i.e. packaged component. Moreover it may be mounted on the substrate 24 in through-hole or in surface mount technology. The detector 22 comprises a microphone 22.1 disposed within a cavity 22.2. Also disposed within the cavity 22.2 is a reference gas 22.3 which is of the same species as the gas to be sensed and which is disposed within the cavity 22.2. The cavity 22.2 is formed in a similar way as the cavity 21.2 of the emitter module 21 and comprises a recess area formed in the substrate 24, wherein the recess area is confined by a laterally closed elevation of the substrate 24 in the same manner as the recess area of the emitter 21. Similarly, the laterally closed elevation comprises an upper coplanar surface on which a light entrance window 22.4 is disposed. The light entrance window 22.4 is disposed in such a way that the reference gas 22.3 is hermetically sealed within the cavity 22.2. The microphone 22.1 may be formed by a MEMS-microphone. The microphone 22.1 may be mounted on a surface of the substrate 24 by through-hole or surface mount technology. The detector 22 may comprise further electronic devices 22.5 like, for example, a logic integrated circuit chip or an ASIC chip. The housing 23 may comprise an inner reflective wall 23.1 which is highly reflective for light emitted by the light emitter 21.1. The geometry of the inner surface of the sensor housing 23 may have an ellipsoidal form, wherein the light emitter 21.1 and the microphone 22.1 may be disposed in the focal points of the ellipse.

FIG. 2B shows an example of a photo-acoustic gas sensor similar to the example of FIG. 2A. The photo-acoustic gas sensor module 30 of FIG. 2B comprises an emitter module 31 and a detector module 32 both of which being mounted on a substrate 34 by through-hole technology. Both of the emitter module 31 and the detector module 32 comprise metallic housings 31.1 and 32.1, respectively. The emitter module 31 further comprises a light outlet window 31.2 formed in an upper surface of the metallic housing 31.1, and the detector module 32 comprises a light inlet window 32.2 formed in an upper surface of the metallic housing 32.1. The photo-acoustic gas sensor module 30 of FIG. 2B further comprises a sensor housing 33 which can be formed in the same way as the housing 23 of the photo-acoustic gas sensor module 20 of FIG. 2A. In particular the sensor housing 33 may also comprise an inner reflective wall 33.1 which is highly reflective for light emitted by the emitter module 31. The geometry of the inner surface of the sensor housing 33 may have an ellipsoidal form, wherein the emitter module 31 and the detector module 32 may be disposed in the focal points of the ellipse. The photo-acoustic gas sensor module 30 may further comprise a further electronic device 35 which can be a logic integrated circuit chip or an ASIC chip. The substrate 34 can be a multi-layer printed circuit board (PCB).

FIGS. 3A and 3B show two different examples of housings which can be employed to efficiently guide the light emitted by the light emitter. FIG. 3A shows again the photo-acoustic gas sensor module 20 of FIG. 2A depicting therein three different light paths of light emitted by the light emitter 21.1. It is shown that due to the positioning of the light emitter 21.1 and the detector 22 in the focal points of the ellipse, in whatever directions the light is emitted by the light emitter 21, it will enter the cavity 22.2 of the detector 22 and be focused in an area in a vicinity of the microphone 22.1. FIG. 3B shows a photo-acoustic gas sensor module 40 which differs from the photo-acoustic gas sensor module 20 only in the geometrical form of the inner wall of the sensor housing. The photo-acoustic gas sensor module 40 of FIG. 3B comprises a housing 43 comprising an inner reflective wall 43.1 which comprises two opposed inclined wall sections so that light emitted by the light emitter 41 is reflected at one of the inclined wall sections and thereafter the light beam is reflected by another one of the inclined wall sections in a direction of the detector 42 and the microphone 42.1. FIGS. 3A and 3B show that the light beam enters the cavity 22.2 or 42.2 of the detector module 22 or 42 not directly above the microphone 22.1 or 42.1, respectively. It should be noted that it will only be required that a sufficiently large volume of the reference gas is excited by the light beam so that the pressure pulse emanating from this volume can reach the microphone.

FIGS. 4A and 4B, which correspond to FIGS. 3A and 3B, wherein the difference is the same as between FIG. 2A and FIG. 2B. FIG. 4B shows again the photo-acoustic gas sensor module 30 of FIG. 2B with the sensor housing 33 attached to the substrate 34. The light paths of the light beams emitted by the emitter module 31 correspond to the light paths as shown in FIG. 3A. FIG. 4B shows a photo-acoustic gas sensor module 50 being configured similar to the photo-acoustic gas sensor module 30 with the exception of the housing 53 which is formed like the housing 43 of the photo-acoustic gas sensor module 40 of FIG. 3B. Reference signs 51 and 52 designate the emitter module and the detector module, respectively.

Figure 5A:
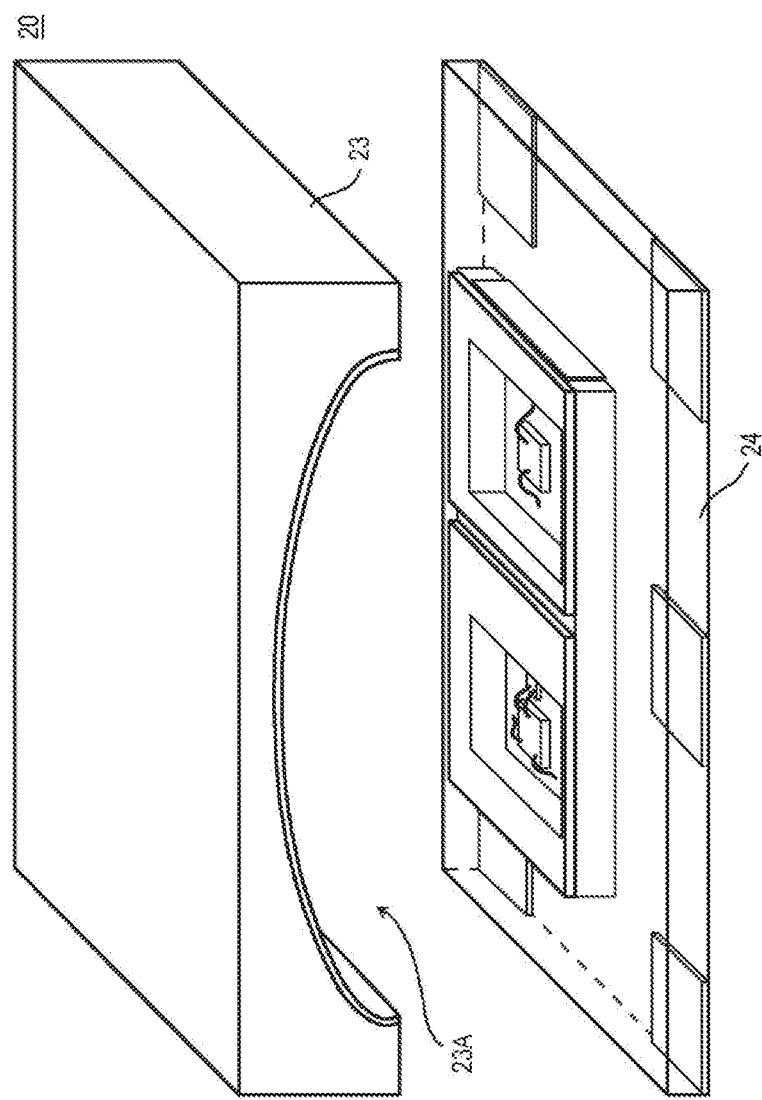

FIGS. 5A and 5B show a perspective view of the photo-acoustic gas sensor module 20 of FIG. 2A. The perspective view makes visible that the housing 23 comprises an opening 23A which opening 23A allows atmospheric gas to enter the interior of the housing 23 and thus to be sensed by the photo-acoustic gas sensor module 20. In the example as shown in FIGS. 5A and 5B, the opening 23A comprises a cross-section which is shaped in the same way as the cross-section of the housing 20 along, for example, a central plane of the housing 20, i.e. the cross-section of the opening 23A has the form of a half ellipsoid. It can be the case that the housing 20 comprises only one opening 23A so that atmospheric gas can enter the interior of the housing 20. FIG. 5B shows a further variant, wherein the housing comprises two opposing openings so that atmospheric gas can not only enter the interior of the housing 23 from two opposing sides but also atmospheric gas can flow through the interior of the housing 23 by entering an opening on one side and leaving through the other opening on the opposing side.

FIG. 6 shows a perspective view of an example of a photo-acoustic gas sensor module. The photo-acoustic gas sensor module 60 of FIG. 6 can be one of the first aspect or the second aspect, wherein the focus in this example lies on the sensor housing 63. As in the previous examples the sensor housing 63 is attached to a substrate 64 thereby forming an interior space in which an emitter (not shown) and a detector (not shown) are disposed. The sensor housing 63 further comprises a gas inlet opening 63A so that atmospheric gas can flow into the interior space to be sensed by the combined effect of the emitter and detector modules as described before. The photo-acoustic gas sensor module 60 of FIG. 6 further comprises a foil 63B which is inserted in the opening 63A and can be fabricated of any material like metal or plastic, for example. The foil 63B can also have a porous structure. The function of the foil 63B is to prevent penetration of humidity and/or particles into the interior space of the module 60 and/or to enable only the penetration of defined gases into the interior space, in particular one specific gas which can be of the same species as the reference gas disposed in the detector module. The foil 63B thus fulfills the function of a filter configured to filter out anything else but the specific gas to be sensed.

Figure 7B:
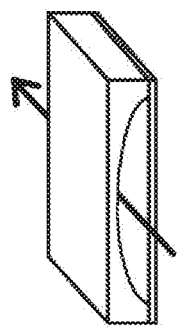
FIGS. 7A through 7C show a perspective representation of an example of a photo-acoustic gas sensor according to the second aspect comprising a sensor housing (shown lifted) having an ellipsoidal inner wall, the same photo-acoustic gas sensor with the housing attached to the substrate and indicating the gas flow, and an example of a photoacoustic gas sensor according to the second aspect having a protective cover covering the opening for preventing penetration of humidity and/or particles and enabling only penetration of defined gases.
Figure 7C:
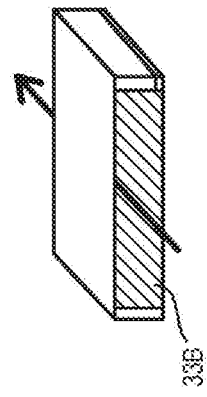
Figure 7A:
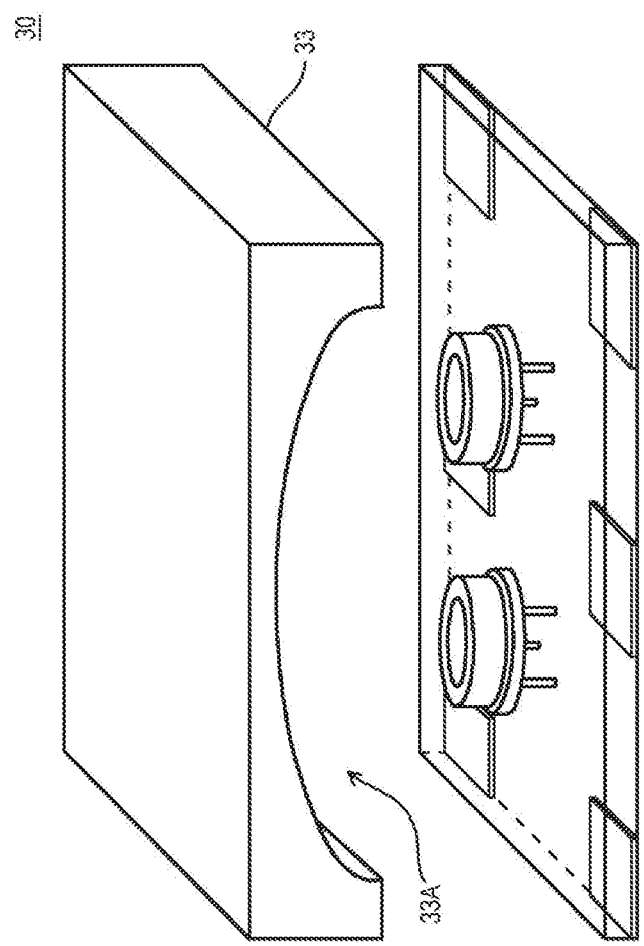

FIGS. 7A through 7C show the photo-acoustic gas sensor module 30 as already shown and explained in connection with FIG. 2B. The way of illustrating the photo-acoustic gas sensor module 30 in FIGS. 7A through 7C is analogous to FIGS. 5A and 5B and likewise shows that the housing 33 comprises a gas inlet opening 33A similar or identical to the gas inlet opening 23A of the photo-acoustic gas sensor module 20 of FIG. 5. The gas inlet opening 33A can be provided on opposing side faces of the housing 33 as shown in FIG. 7B and analogous to FIG. 5B. The gas inlet opening 33A can as well be provided with a foil 33B as shown in FIG. 7C wherein the foil 33B can be similar to the foil 63B shown in FIG. 6.

Figure 8A:
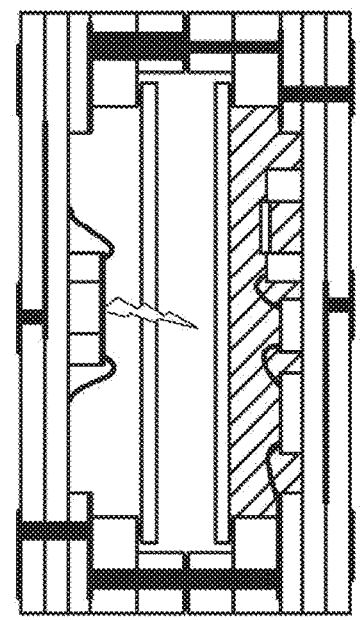
FIGS. 8A through 8D show schematic cross-sectional side view representations of an example of a photo-acoustic gas sensor according to the first aspect, wherein the light emitter and the detector are each mounted on separate ceramic substrates, the modules shown before being mounted together, the gas sensor shown in an assembled state, a perspective representation of the detector module, and a perspective representation of the sensor showing the gas flow.

FIGS. 8A through 8D show an example of a photo-acoustic gas sensor module. The photo-acoustic gas sensor module 70, as shown in FIGS. 8A through 8D, comprises a face-to-face arrangement of emitter and detector. The assembly of the photo-acoustic gas sensor module 70 starts with a separate building-up of a light emitter module 71 and a detector module 72 as depicted in FIG. 8A. The light emitter module 71 comprises a substrate 71.4 similar to the substrate 24 of FIG. 2A. The substrate 71.4 comprises a recess area 71.2 in which a light emitter 71.1 is disposed on a flat lowermost surface of the recess area 71.2. The recess area 71.2 is laterally confined by a ring-like closed elevation of the substrate 71.4 which also allows to have a light outlet window 71.5 being secured thereon. The light outlet window 71.5 can sealingly connected to the substrate 71.4 as shown by the arrow. The detector module 72 likewise comprises a substrate 72.4 similar to the substrate 24 of FIG. 2A comprising a recess area 72.2. The recess area 72.2 is laterally confined by a ring-like closed elevation of the substrate 72.4 which also allows to have a light inlet window 72.5 being secured thereon. The recess area 72.2 enclosed by the ring-like elevation of the substrate 72.4 and the light inlet window 72.5 is filled with a reference gas 72.3 for which reason the light inlet window 72.5 is hermetically sealed to the ring-like elevation of the substrate 72.4 as indicated by the arrow. The recess area 72.2 comprises a lowermost plane surface on which a microphone 72.1 is disposed. Also disposed on the lowermost surface of the recess area 72.2 is at least one further electronic device 72.6 like a logic integrated circuit chip or an ASIC chip.

Figure 8B:
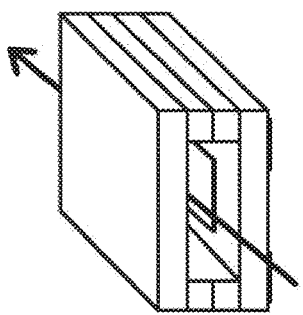
Figure 8C:
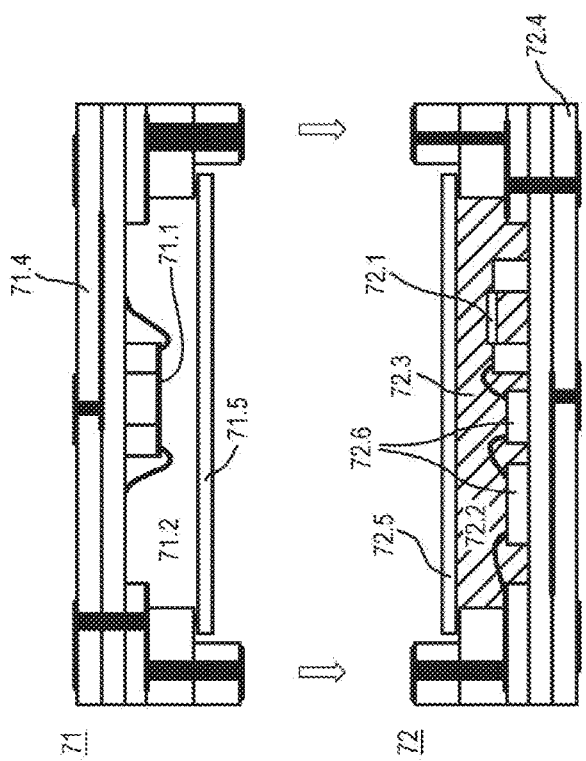

FIG. 8B shows the assembled photo-acoustic sensor module 70, wherein the ring-like elevations of the emitter module 71 and the detector module 72 are attached to each other. In order to detect a gas present in the environmental atmosphere, the area between the light outlet window 71.5 and the light inlet window 72.5 must have access to the outside. This can be achieved by forming one or both of the elevations of the emitter module 71 and the detector module 72 in such a way that an uppermost layer thereof is not formed as a closed ring but leaves at least one open side or two opposing open sides as shown in FIG. 8C (the arrow indicates one of the elevations) and 8D.

FIGS. 9A through 9C show an example of a photo-acoustic gas sensor module. The photo-acoustic gas sensor module 80 of FIGS. 9A through 9C is similar to the photo-acoustic sensor module 70 of FIGS. 8A through 8D, and differs from the latter essentially in the way the light emitter module is provided, wherein the detector module is similar or identical to that one of FIGS. 8A through 8D. The light emitter module 81 of the photo-acoustic gas sensor module 80 comprises a substrate 81.1 which can, for example, be a PCB-like laminate on which a packaged light emitter device 81.2 is mounted. The light emitter device 81.2 can be mounted on the substrate 81.1 by surface mount technology as depicted in FIG. 9A or alternatively by through-hole technique. The light emitter module 81 is then attached to the elevated portion of the substrate 82.4 of the detector module 82 to form the assembled photo-acoustic gas sensor module 80 as shown in FIG. 9B. To provide access to the area between the light emitter module 81 and the light inlet window 82.5 of the detector module 82, can be accomplished in the same way as explained in connection with FIGS. 8A through 8D, namely by forming an upper layer of the elevations of the substrate 82.4 in such a way that it is not ring-like closed as is indicated by the arrow in FIG. 9C.

FIG. 10 shows an example of a photo-acoustic gas sensor module 90 which is similar to the photo-acoustic gas sensor module 80 as shown in FIG. 9B. The photo-acoustic gas sensor module 90 of FIG. 10 does not comprise a substrate on which the light emitter module 91 is attached. Instead the light emitter module 91 comprises external lead elements 91.1 which are attached to the upper plane surfaces of the elevated portions of the substrate 92.4 of the detector module 92 and electrically connected to contact areas disposed on these upper plane surfaces.

Figure 11A:
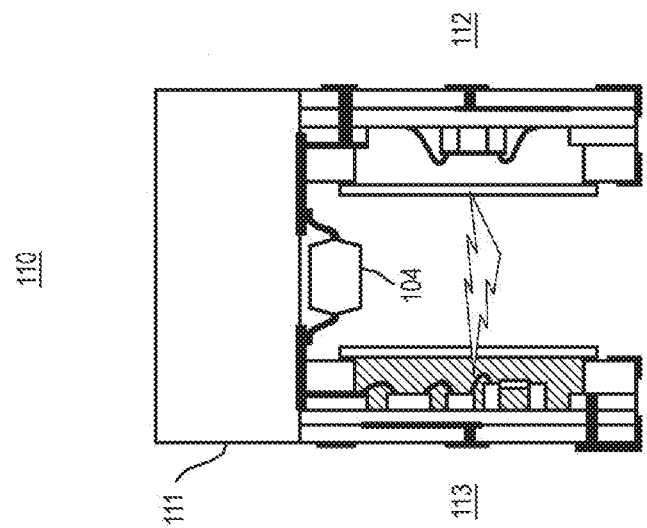
FIGS. 11A and 11B show schematic cross-sectional side view representations of examples of photo-acoustic gas sensors according to the first aspect, wherein the emitter and the detector are each mounted on a ceramic substrate and both ceramic substrates are mounted on a board, wherein in the first example the board is configured as a surface mount device (SMD), and wherein in the second example the ceramic substrates are configured as an SMD device.
Figure 11B:
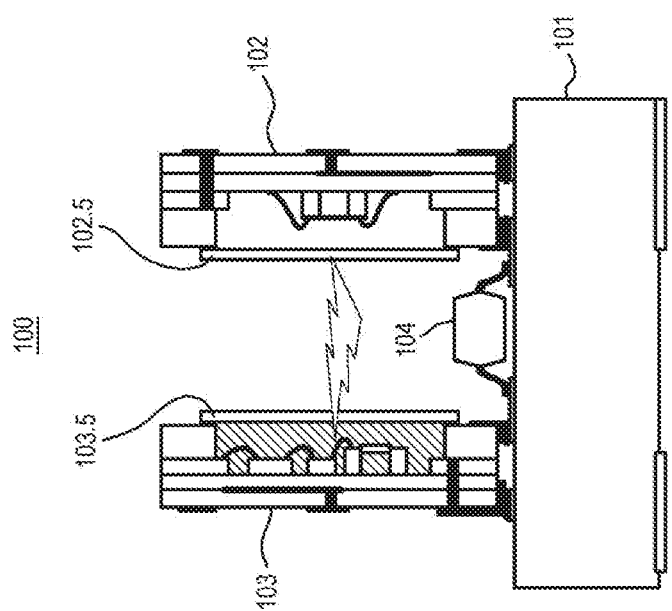

FIGS. 11A and 11B show examples of photo-acoustic gas sensor modules 100 and 110. The photo-acoustic gas sensor module 100 comprises a substrate 101 which can be a PCB or PCB-like laminate. On an upper surface of the substrate 101 a light emitter module 102 and a detector module 103 are mounted in a face-to-face configuration, i.e. so that the light outlet window 102.5 of the light emitter module 102 and the light inlet window 103.5 of the detector module 103 are facing each other. Both modules 102 and 103 are mounted with their side faces onto the upper surface of the substrate 101. In particular, the modules 102 and 103 comprise contact elements on their side faces and are mounted with these contact elements on respective contact areas on the upper surface of the substrate 101 in a surface mount technology. In addition, a further electronic device 104 like, for example, a packaged integrated circuit chip can be mounted on the upper surface of the substrate 101 and connected with respective contact areas thereon. The photo-acoustic gas sensor module 100 is configured as a surface mount device in such a way that electrical contact areas are applied on a lower surface of the substrate 101 so that the photo-acoustic gas sensor module 100 as a whole can be mounted on a substrate like a PCB in a surface mount technology.

The photo-acoustic gas sensor module 110 of FIG. 11B is similar to the one shown in FIG. 11A and is also configured as a surface mount device. The difference to the module 100 of FIG. 11A is that electrical contact areas are applied on side faces of the modules 112 and 113 remote from the substrate 111 so that the module 110 can be mounted on a substrate like a PCB with these side faces of the modules 112 and 113 instead of with the substrate 111. Reference sign 114 denotes a further chip similar to chip 104 of FIG. 11A.

FIGS. 12A and 12B comprise two different examples of photo-acoustic gas sensor modules in a cross-sectional side view representation (left-sided pictures) and in a top view representation (right-sided pictures), respectively. FIG. 12A shows a photo-acoustic gas sensor module 120 comprising a light emitter module 121 and a detector module 122. The module is similar to the module 90 of FIG. 10 with the exception that between the light emitter module 121 and the detector module 122 an intermediate substrate 125 is inserted, i.e. the intermediate substrate 125 comprising a recess area 125A and the light emitter module 121 is electrically connected with its external leads to electrical contact areas on an upper surface of the intermediate substrate 125 and the detector module 122 is connected with electrical contact areas on its elevations to electrical contact areas on a lower surface of the intermediate substrate 125. As can be seen in the top view of FIG. 12A, the modules 121 and 122 are mounted in such a way on the intermediate substrate 125 that they face each other through the recess area 125A.

Figure 8D:
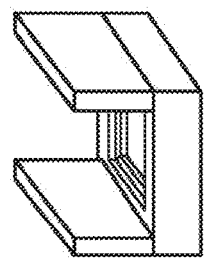

The photo-acoustic gas sensor module 130 of FIG. 12B is similar to the module 70 of FIGS. 8 through 8D, and comprises a light emitter module 131 and a detector module 132. The difference to the module 70 of FIGS. 8A through 8D is that in the same way as with module 120, an intermediate substrate 135 is disposed between modules 131 and 132. The modules are facing each other through the recess area 135A of the intermediate substrate 135 in the same way as was shown and explained with the module 120 of FIG. 12A.

FIGS. 13A through 13C show examples of photo-acoustic gas sensor modules 140 and 150. The photo-acoustic gas sensor module 140 comprises a light emitter module 141 and a detector module 142. The module 140 is similar to the module 30 of FIG. 2B with the following differences. The light emitter module 141 and the detector module 142 are connected with their leads in a through-hole technique to a substrate 144, wherein the leads are bent so that the modules 141 and 142 are arranged face-to-face with each other which means that a light outlet window 141.5 and a light inlet window 142.5 are facing each other. This means that no particular geometry of the housing 143 is needed. The housing 143 can be configured as a simple rectangular shape cover. As shown in FIG. 13C the housing 143 should have an opening on at least one of its side faces so that atmospheric gas can enter the interior of the housing 143. The housing 143 is mounted onto the substrate 144. A further electronic device 145 can be mounted on the substrate 144.

The photo-acoustic gas sensor module 150 of FIG. 13B is similar to the module 140, the module 150 also comprising a light emitter module 151 and a detector module 152 in a face-to-face spatial relationship, and a housing 153 similar to the housing 143. The difference to the module 140 is that the modules 151 and 152 are mounted onto a substrate 154 in a surface mount technique in such a way that lower portions of the leads of the modules 151 and 152 are bent so that they are oriented horizontally. With these horizontal portions the leads are mounted on electrical contact areas on the inner surface of the substrate 154.

Figure 14B:
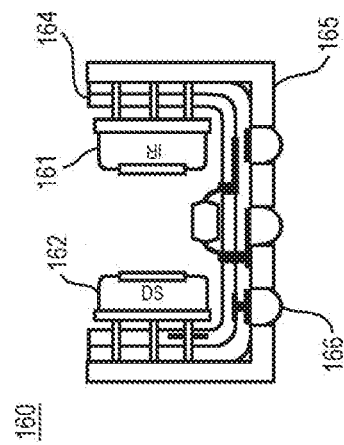
FIGS. 14A and 14B show schematic cross-sectional side view representations of an example of a photo-acoustic gas sensor according to the second aspect, wherein the emitter module and the detector module are mounted on a flexible substrate, shown before its assembly by bending the flexible substrate and inserting it into a rigid housing, and applying solder balls into openings of the rigid housing to form a ball grid configuration.
Figure 14A:
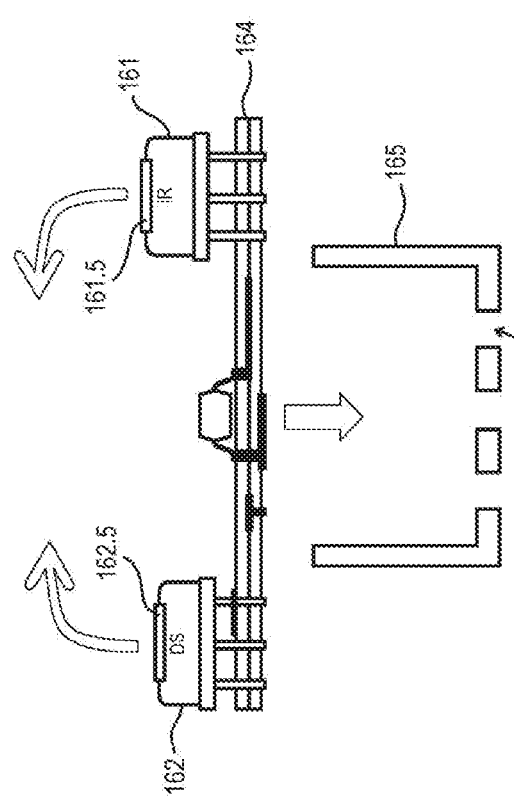

FIGS. 14A and 14B show an example of a photo-acoustic gas sensor module 160. The module 160 comprises a light emitter module 161 and a detector module 162. Both modules 161 and 162 are mounted in through-hole technique to a flexible (PCB) substrate 164. As shown by the arrows the flexible substrate 164 can be bent in such a way that the modules 161 and 162 are facing each other, i.e. the light outlet window 161.5 and the light inlet window 162.5 are facing each other. Afterwards the intermediate product can be inserted into a rigid substrate 165 which comprises openings 165A. Finally solder balls 166 are applied into the openings 165A, the solder balls 166 being connected with electrical contact areas at the lower surface of the flexible substrate 164. The assembled module 160 can be mounted with the solder balls 166 on a substrate like a printed circuit board.

Figure 15:
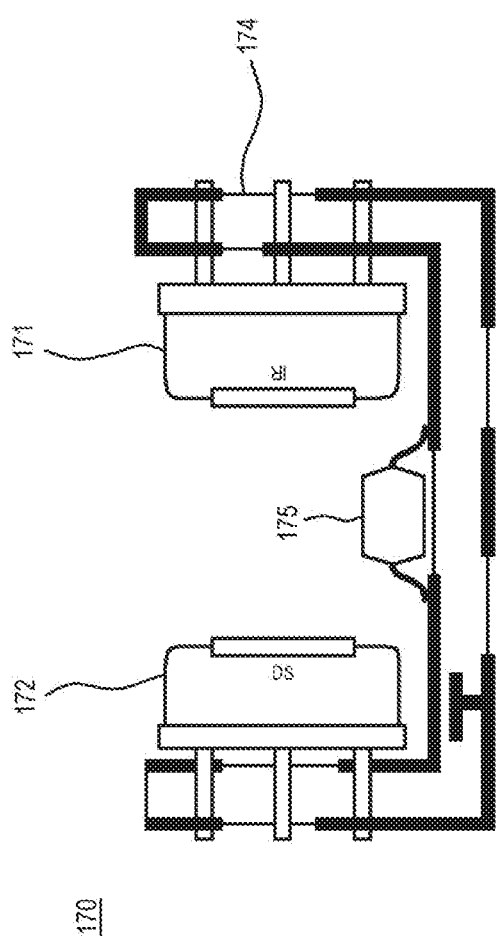
FIG. 15 shows a schematic cross-sectional side view representation of an example of a photo-acoustic gas sensor according to the second aspect, wherein the emitter module and the detector module are mounted in a face-to-face configuration within a rigid housing comprising vias and external contact areas to form a surface mount device (SMD) configuration.

FIG. 15 shows an example of a photo-acoustic gas sensor module 170. The module 170 comprises a light emitter module 171 and a detector module 172 which are both mounted on a rigid multi-layer substrate 174 by through-hole technique. The substrate 174 comprises a U-shaped form wherein the modules 171 and 172 are secured to the inner faces of the side bars of the U-shape. The module 170 also comprises electrical contact areas on the lower surface of the horizontal part so that it can be attached to a PCB board with surface mount technique. A further electronic device 175 is mounted on the inner horizontal surface of the substrate 174.

Figure 16A:
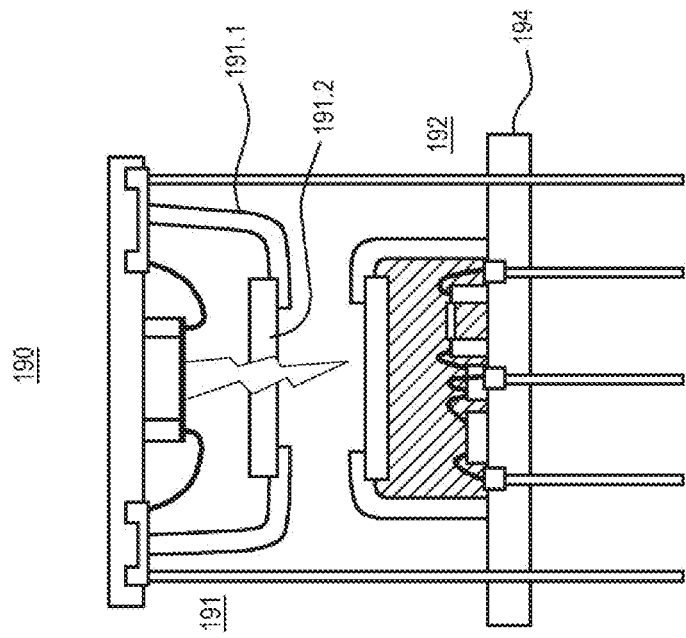
FIGS. 16A and 16B show schematic cross-sectional side view representations of examples of photo-acoustic gas sensors according to the second aspect, wherein the emitter module is disposed above the detector module and both modules are connected with their leads to a substrate in through-hole technique, wherein in the first example the emitter module is configured to emit light through a window inserted in its substrate, and wherein in the second example the emitter module is configured to emit light through a window inserted in its housing.
Figure 16B:
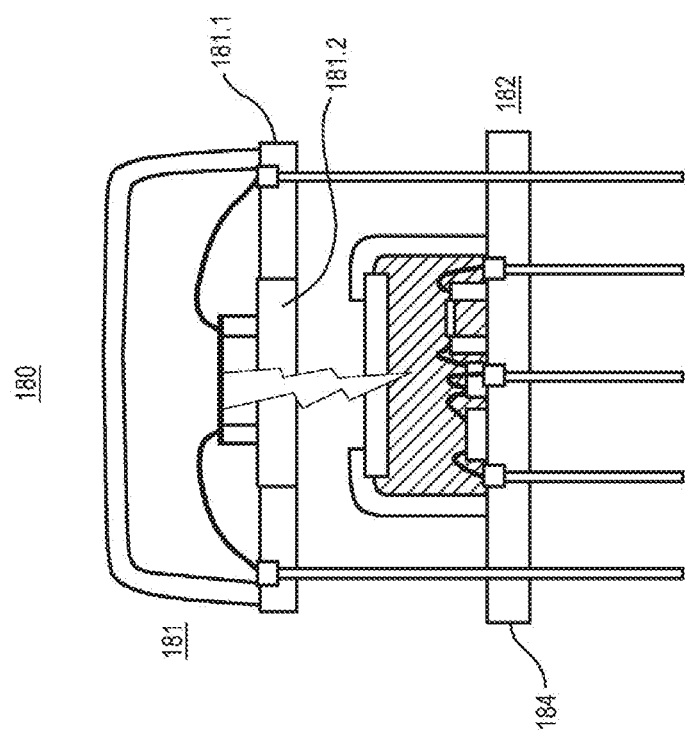

FIGS. 16A and 16B show examples of photo-acoustic gas sensor modules 180 and 190. The module 180 of FIG. 16A comprises a light emitter module 181 and a detector module 182 which are arranged in a way that the light emitter module 181 is disposed above the detector module 182 and both modules are electrically connected to a substrate 184 by through-hole technique. The light emitter module 181 is configured so that the light is emitted through a light outlet window 181.2 which is inserted in a substrate 181.1. The module 190 of FIG. 16B is similar to the module 180 of FIG. 16A. The difference is that the light emitter module 191 is arranged upside down so that the light is emitted through a light outlet window 191.2 which is inserted in the housing 191.1. Both modules 191 and 192 are mounted on a substrate 194 in through-hole technique.

Figure 17:
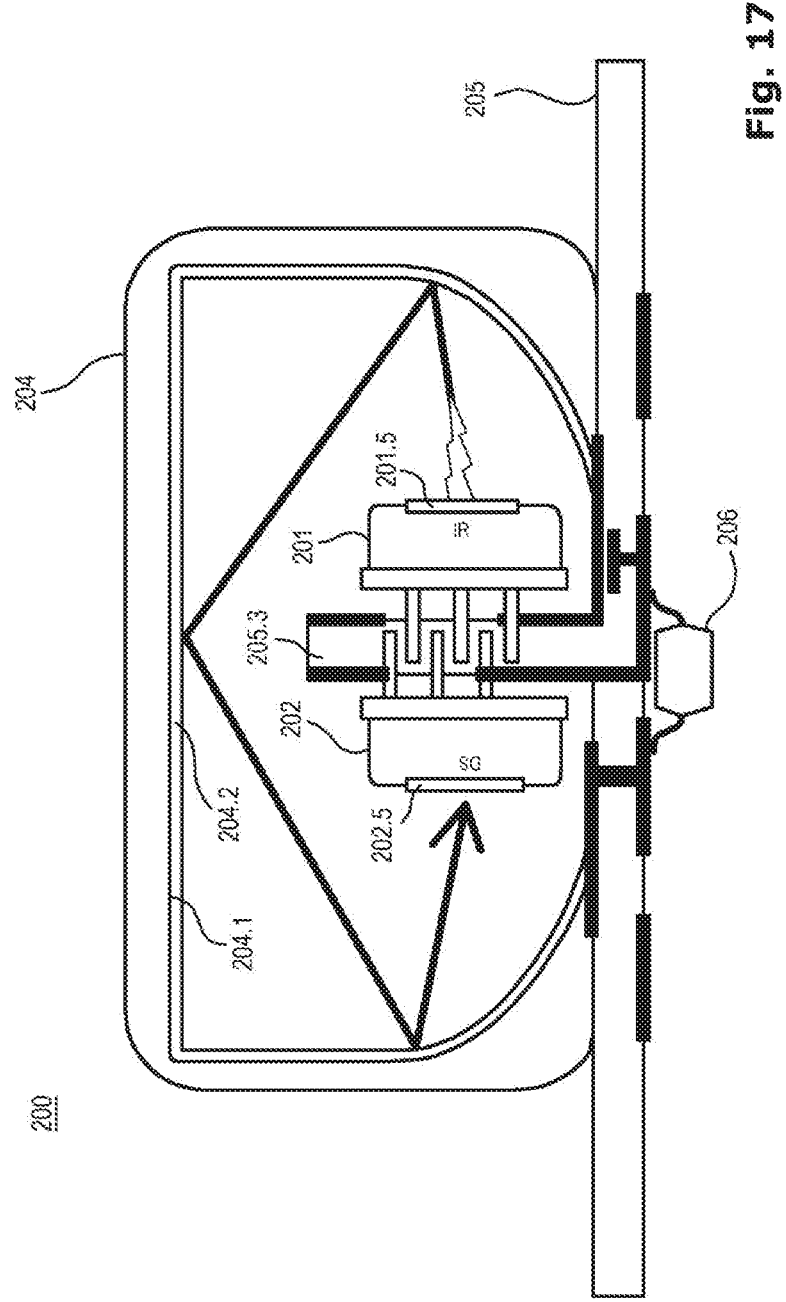
FIG. 17 shows a schematic cross-sectional side view representation of an example of a photo-acoustic gas sensor according to the second aspect in which the emitter module and the detector module are disposed within a housing and with their light outlet and light inlet openings facing away from each other, the housing comprising a reflective inner wall and connected to a substrate in a surface mount device (SMD) configuration.

FIG. 17 shows an example of a photo-acoustic gas sensor module 200 comprising a light emitter module 201 and a detector module 202. The modules 201 and 202 are arranged with their light outlet and light inlet windows 201.5 and 202.5 facing away from each other. The modules 201 and 202 are mounted within a housing 204 which comprises an inner wall 204.1 being covered with a reflective layer 204.2. The modules 201 and 202 are mounted on an upright portion 205.3 of a substrate 205 in a through-hole technique. The housing 204 is mounted onto the substrate 205. A further electronic device 206 like, for example, a logic integrated circuit chip or an ASIC chip, is mounted on a lower surface of the substrate 205. The arrow illustrates the way of the light beam through the interior of the housing 204. One advantage of the module 200 is that the path of the light beam is rather long if compared with previously shown examples. Such a long path is advantageous as the light will be more strongly absorbed by the gas in the interior of the housing so that the sensitivity of the module 200 is increased.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A photo-acoustic gas sensor, comprising:
   a light emitter unit comprising a stationary light emitter configured to emit a beam of light pulses with a predetermined repetition frequency and a wavelength corresponding to an absorption band of a gas to be sensed; and
   a single detector unit comprising a microphone,
   wherein the light emitter unit is arranged so that the beam of light pulses traverses an area configured to accommodate the gas and the single detector unit is arranged so that the microphone can receive a signal oscillating with the repetition frequency,
   wherein the detector unit is disposed on a first substrate within a hermetically sealed chamber, wherein the hermetically sealed chamber comprises a light entrance window opposite from the first substrate and a reference gas within the hermetically sealed chamber, and
   wherein the light emitter unit is disposed on a second substrate that is outside of the hermetically sealed chamber and is arranged face-to-face with the first substrate.

2. The photo-acoustic gas sensor of claim 1, wherein the reference gas is of the same species as the gas to be sensed.

3. The photo-acoustic gas sensor of claim 1, wherein the repetition frequency lies within an audio frequency range.

4. The photo-acoustic gas sensor of claim 1, wherein the stationary light emitter comprises one or more of a black-body radiator, a lamp, a resistor, a diode, and a laser.

5. The photo-acoustic gas sensor of claim 1, wherein the light emitter unit has a tunable wavelength emission range.

6. The photo-acoustic gas sensor of claim 1, wherein the gas to be sensed is one of $CO_2$, $NO_x$, $H_2O$, $O_2$, $N_2$, $CH_4$ and alcohol.

7. A photo-acoustic gas sensor module, comprising:
   a stationary light emitter configured to emit a beam of light pulses to be absorbed by a gas; and
   a single microphone configured to receive a signal oscillating with a repetition frequency of the light pulses,
   wherein the detector unit is disposed on a first substrate within a hermetically sealed chamber, wherein the hermetically sealed chamber comprises a light entrance window opposite from the first substrate and a reference gas within the hermetically sealed chamber, and
   wherein the microphone is disposed on a second substrate that is outside of the hermetically sealed chamber and is arranged face-to-face with the first substrate.

8. The photo-acoustic gas sensor module of claim 7, wherein the photo-acoustic gas sensor module is configured as a surface mount device.

9. The photo-acoustic gas sensor module of claim 7, wherein the stationary light emitter is configured to emit infrared light of a wavelength corresponding to an energy of a rotational or vibrational band of a molecule of the gas.

* * * * *